United States Patent [19]
Bergfried et al.

[11] Patent Number: 5,654,457

[45] Date of Patent: Aug. 5, 1997

[54] METHOD FOR SYNTHESIZING ALKYL TIN FLUORIDES

[75] Inventors: Stefan Bergfried, Essen; Dieter Guhl, Hattingen; Sven Uwe Vallerien, Essen, all of Germany

[73] Assignee: Th. Goldschmidt AG., Essen, Germany

[21] Appl. No.: 673,462

[22] Filed: Jul. 1, 1996

[30] Foreign Application Priority Data

Aug. 18, 1995 [DE] Germany .................. 195 30 434.9

[51] Int. Cl.$^6$ ...................................... C07F 7/22
[52] U.S. Cl. .................. 556/89; 556/95; 556/104
[58] Field of Search ..................... 556/95, 104, 88, 556/89

[56] References Cited

U.S. PATENT DOCUMENTS

| | | | |
|---|---|---|---|
| 4,694,091 | 9/1987 | Kerherve | 556/104 |
| 4,987,245 | 1/1991 | Bonneau | 556/104 |

*Primary Examiner*—C. Warren Ivy
*Assistant Examiner*—Jean F. Vollano
*Attorney, Agent, or Firm*—Anderson Kill & Olick P.C.

[57] ABSTRACT

The application relates to a method for the synthesis of finely particulate organic tin (oxy) fluorides by reacting mono-organic or diorganic tin oxides or hydroxides with fluoric acid, the reaction being carried out in the presence of surface active compounds.

6 Claims, No Drawings

METHOD FOR SYNTHESIZING ALKYL TIN FLUORIDES

FIELD OF INVENTION

The invention relates to a method for synthesizing finely particulate alkyl tin fluorides or oxyfluorides, particularly those, which are suitable for the production of fluoride-doped tin oxide layers on glass, glass ceramic and enamel.

BACKGROUND INFORMATION AND PRIOR ART

The coating of substrates with doped tin oxides is well known whereby the electrical resistance of the surface, so coated, is decreased and the infrared reflection is increased. Technically, these physical properties are used for heat-absorbing glazing or also for the two-dimensional heating of panes, such as windshields or rear windows of cars and refrigerated counter glazing.

In order to produce such layers, suitable tin compounds (basic compounds) are brought, preferably simultaneously with a doping agent, into contact with the glass surface, which has been heated to 400° to 800° C. The basic tin compound forms a coherent tin(IV) oxide layer on the surface of the glass, the glass ceramic or the enamel. Particularly fluorine, as doping agent, increases the electrical conductivity and brings about the high infrared reflection. The use of powdery dibutyl tin difluoride is described in the EP-A-0 039 256 and EP-A-0 511 044.

The coating itself can become homogeneous only if the powder flows well in the coating equipment and does not agglomerate within it. Due to hygroscopy, alkali and alkaline earth impurities, in particular, are responsible for the agglomeration. Furthermore, alkali ions interfere with the formation of the electrically conductive and, with that, infrared-reflecting layer, since they act as defect sites for the free electrons, necessary for the charge transport, and, with that, lead to a reduction in the functional properties of the layers.

Dibutyl tin difluoride (DBTF) usually is synthesized from dibutyl tin dichloride (DBTCL) and potassium fluoride in a water/alcohol solvent. Furthermore, sodium fluoride or other alkali or alkaline earth fluorides are also used instead of potassium fluoride; however, they lead to the problems mentioned above.

In the U.S. Pat. No. 4,694,091, a method is described for synthesizing DBTF from an alcoholic solution of DBTCL and an aqueous solution of ammonium difluoride. At the same time, the initially-formed DBTF is dissolved again in a suitable solvent, such as methanol, and recrystallized at least once. During the recrystallization, silica gel, preferably Aerosil® 972, is added in order to support the formation of the desired particle size. During the subsequent crystallization, a temperature jump of at least 45° C. is regarded as necessary and achieved by pouring or even spraying the hot solution into a cooled, clean solvent. In a subsequent step of the process, washing is repeated once more with chlorinated hydrocarbons, such as methylene chloride or trichlorotrifluoroethane. With this effort, it is then possible to obtain a DBTF powder with a suitable average particle size between 15 and 25 µm. This powder consists of spherical particles and is thus macroscopically flowable and can be metered out.

Such a method is not satisfactory from several points of view. Particularly, the expensive conduct of the process and the use of large amounts of methanol and chlorinated hydrocarbons are disturbing features.

A method for reacting dibutyl tin diacetate with hydrofluoric acid is described in U.S. Pat. No. 4,322,363.

In the EP-A-0 364 337, a synthesis method is described, for which the DBTCL is reacted with hydrofluoric acid in a suitable solvent. The further steps of the process comprise the use of o-dichlorobenzene for the purpose of driving out excess hydrofluoric acid and crystallizing the solution, which had previously been heated to 120° C., by cooling. The product must subsequently be washed once again with halogenated hydrocarbons.

It is furthermore known to those skilled in the art that organic tin fluorides can also be obtained directly by the reaction of organic tin oxides with hydrofluoric acid. With respect to the starting compounds, this is the most direct way.

In practice, on the other hand, this method is unsuitable, since it does not lead to the desired powder properties of flowability and particle size and instead produces agglomerated, practically no longer flowable, pasty powders.

Since organic tin oxides are hydrophobic compounds, the reaction in aqueous media frequently is difficult, because the degree of conversion achieved is not sufficient. Frequently, therefore, solvent mixtures such as water/alcohol are used, in order to achieve a corresponding degree of conversion. Accordingly, the use of organic solvents is also necessary for this method. The necessary working up increases the costs of the process. Furthermore, the products obtained from this process tend to sinter or adhere during drying, so that the fineness of the particles, required for the application, is not achieved and such products accordingly cannot be used for coating glass.

All the methods mentioned prove to be technically complicated. In addition, expensive purification steps are required, generally involving the use of halogenated hydrocarbons or expensive starting materials. There was therefore a need for a suitable method, which avoids the disadvantages mentioned above. These problems are solved by the inventive synthesis method by which, in particular, an alkali-free and alkaline earth-free DBTF with spherical particles of suitable average particle size is achieved.

SUMMARY OF THE INVENTION

Pursuant to the invention, the problem is solved owing to the fact that, for the synthesis of finely particulate organic tin (oxy) fluorides, mono-organic or diorganic tin oxides are reacted with hydrofluoric acid in the presence of surface-active compounds.

The mono-organic or diorganic tin oxides or hydroxides, used as starting compounds, are known compounds and described, for example, in M. Dub, Organometallic Compounds, Vol. II, Springer-Verlag, (1967), pages 367–377. Aliphatic tin compounds are preferred because of the danger of liberating aromatic compounds from aryl tin compounds under the processing conditions.

As diorganic tin oxides, dioctyl tin oxide or the particularly preferred dibutyl tin oxide (DBTO) can, for example, be used. As mono-organic tin compounds, methyl, propyl, butyl or octyl tin oxide, for example, or further homologs come into consideration. The corresponding hydroxides, such as $Bu_2Sn(OH)_2$, can likewise be used.

The organic groups on the tin may contain ester groups. In this connection, particularly compounds of the $(ROOCCH_2CH_2)_2SnO$ type, in which R represents an alkyl group, come into consideration.

The organic tin starting compounds are reacted with a stoichiometric or substoichiometric amount of hydrofluoric acid in water as solvent to form the desired end product, surface active compounds being added to the aqueous solution.

For the stoichiometric reaction, all Sn—O bonds are replaced by the corresponding Sn—F bonds to obtain the corresponding organic tin fluorine compounds, such as $BuSnF_3$ or $(Prop)_2SnF_2$.

For the substoichiometric reaction with hydrofluoric acid, organic tinoxyfluoride is obtained, for example, $(Bu)_2FSn—O—SnF(Bu)_2$.

The surface active compounds surprisingly enable the hydrophobicity of the organic tin oxide to be overcome to such an extent that it can be dispersed homogeneously in water, so that practically a complete conversion is attained.

As surface active compounds, those wetting agents come into consideration, which have a rapid wetting capability and a high degree of stability with respect to hydrofluoric acid.

Wetting agents have a wetting time of less than 12 seconds at 25° C. in a 0.1% solution (measured by the ASTM D 2281 skein test, with a hook weight of 3 g and using a cotton strand of 5 g).

In particular, these can be fluorinated surfactants, silane surfactants, fatty alcohol alkoxylates or nonylphenol alkoxylates, an ethyleneoxide ("EO") and/or propyleneoxide ("PO") content of 6 to 12 being particularly effective.

The wetting agents are used in different amounts, depending on the type. For the particularly preferred type of surfactants, amounts of 0.01 to 0.5% by weight, based on the amount of water used, have proven to be satisfactory.

The silane surfactants and the fatty alcohol alkoxylates are particularly advantageous, since they can be degraded readily by biological means and thus not lead to problems during the treatment of effluent.

The inventive method has a special advantage in that it enables particularly fine particulate, alkyl tin fluorides to be synthesized, which are suitable for pyrolytically producing fluorine-doped tin oxide layers on glass, glass ceramic and enamel.

In order to arrive at the desired product, the starting material is an organic tin oxide compound with a defined particle size. The average particle size of the product is somewhat higher than that of the starting material, as is the upper limit of the particle size.

It is advisable to select an average particle size as well as an upper limit to the particle size of the starting material, which is at least 10 μm less than the aimed-for values of the product.

For example, in order to arrive at organic tin fluorides with an average particle size of 50 to 70 μm, as used in the glass industry, it is advisable to start out from an organic tin oxide having an average particle size of about 40 μm.

In the method, the use of surface active compounds offers the following advantages:

1. problem-free dispersability of the organic tin oxide;
2. easier filtration and reduction in the filtration time;
3. reduction in the dusting of the dry product, since the electrostatic charging of the powder particles is decreased clearly;
4. any amounts of surfactant, adhering to the surface of the product, do not interfere with the application because they are contained in such small amounts; and
5. optionally, these are pyrolyzed from the hot glass surface without leaving a residue.

Furthermore, the method offers the advantage of a clean, aqueous solvent, with which the working-up costs can be reduced drastically. It is furthermore possible to use the reaction water once again for a new batch, since there are no waste materials. Moreover, there is no need to add crystallization aids.

The inventive method is described in the following. It is understood that the following examples are provided by way of illustration and not by way of limitation. Dibutyl tin oxide (DBTO), which is inexpensive, is used as organic tin starting material. Half of it is suspended in deionized water with the aid of a nonionic surfactant. Subsequently, the reaction is carried out with substoichiometric amounts of hydrofluoric acid to form DBTF, which is washed once with deionized water and dried under vacuum. The so-obtained product is distinguished by good flowability and a spherical particle shape with a suitable average particle size.

To attain as narrow a particle size distribution as possible (90% between 5 μm and 40 μm) with an upper particle size limit of ≦65 μm, it is advantageous to use a DBTO with an upper particle size limit of 25 μm.

EXAMPLE 1

To a 2 L flask, 1000 mL of deionized water and 1 g of a $C_8$ fatty alcohol ethoxylate (6 EO units) are added and 249 g of DBTO are suspended in the solution at about 20° C. Subsequently, 190 g of a 40% hydrofluoric acid solution are added. The temperature rises to about 32° C. After 60 minutes, a further 249 g of DBTO are added. In the course of the next 30 minutes, the temperature remains at about 35° C. At the end of the reaction, the suspension is filtered. According to wet chemical analysis, the aqueous filtrate contains 0.06% of fluoride. The filter cake is dried at 60° C. in a vacuum oven at a vacuum of 30 mm Hg. A yield of 97.5% is obtained. The bulk density of the material is 0.18 g. The average particle size is about 20 μm and the material flows very well.

EXAMPLE 2

Synthesis of Monobutyl Tin Trifluoride

To a reaction vessel, 400 g of water and, with stirring, 2 g of nonylphenol ethoxylate (8 EO units) are added. Subsequently, 208.8 g of monobutyl tin oxide, with an average particle size of 50 μm, are stirred in and treated with 150 g of a 40% solution of hydrofluoric acid, which is added in portions.

After the exothermic reaction has declined, the reaction is allowed to continue for 2 hours. Hereupon, the suspension is filtered and dried for 8 hours at 90° C.

The resulting product is a free-flowing powder with an average particle size of 65 μm. The MBTF contains 49% tin and 23% fluorine.

EXAMPLE 3

Synthesis of Monobutyl Tin Oxide Fluoride

To a reaction vessel, 400 g of water are added and mixed with 2 g of nonylphenol ethoxylate with stirring. Subsequently, 208.8 g of monobutyl tin oxide, with an average particle size of 50 μm, are stirred in and treated with 100 g of a 40% hydrofluoric acid solution added in portions.

After the exothermic reaction has declined, the reaction is allowed to continue for 2 hours. Hereupon, the suspension is filtered and dried for 8 hours at 90° C.

The resulting product is a free-flowing powder with an average particle size of 60 to 70 μm. The butyl tin oxide fluoride contains 50.8% tin and 15.2% fluorine.

EXAMPLE 4

The Synthesis of Dibutyl Tin Difluoride

To a reaction vessel, 400 g of water are added and mixed with stirring with 2 g of nonylphenol ethoxylate. Subsequently, 498 g of dibutyl tin oxide, with an average particle size of 25 μm are stirred in and treated with 200 g of a 40% solution of hydrofluoric acid, which is added in portions.

After the exothermic reaction has declined, the reaction is allowed to continue for 2 hours. Hereupon, the suspension is filtered and dried for 6 hours at 90° C.

The resulting product is a free-flowing powder with an average particle size of 40 μm. The analysis of DBTF reveals 44% tin and 14.4% fluorine.

EXAMPLE 5

Synthesis of Dibutyl Tin Oxide Fluoride

To a reaction vessel, 400 g of water are added and mixed with stirring with 2 g of nonylphenol ethoxylate. Subsequently, 498 g of dibutyl tin oxide, with an average particle size of 25 μm are stirred in and treated with 150 g of a 40% solution of hydrofluoric acid, which is added in portions.

After the exothermic reaction has declined, the reaction is allowed to continue for 2 hours. Hereupon, the suspension is filtered and dried for 8 hours at 90° C.

The resulting product is a free-flowing powder with an average particle size of 40 μm. The analysis of the product reveals a tin content of 44.7% and a fluorine content of 9.5%.

EXAMPLE 6

Synthesis of Dioctyl Tin Difluoride

To a reaction vessel, 400 g of water are added and mixed with stirring with 2 g of nonylphenol ethoxylate. Subsequently, 361.1 g of dioctyl tin oxide, with an average particle size of 50 μm are stirred in and treated with 100 g of a 40% solution of hydrofluoric acid, which is added in portions.

After the exothermic reaction has declined, the reaction is allowed to continue for 2 hours. Hereupon, the suspension is filtered and dried for 12 hours at 90° C.

The resulting product is a free-flowing powder with an average particle size of 75 μm. The dioctyl tin difluoride contains 30.6% tin and 9.4% fluorine.

EXAMPLE 7

Comparison Example

(Not of the Invention)

Synthesis of Dibutyl Tin Difluoride

To a reaction vessel, 400 g of water are added and mixed with stirring with 200 g of a 40% solution of hydrofluoric acid. Subsequently, 498 g of dibutyl tin oxide, with an average particle size of 25 μm are stirred in.

After the exothermic reaction has declined, the reaction is allowed to continue for 2 hours. Hereupon, the suspension is filtered and dried for 8 hours at 90° C.

The resulting product is of pasty, partially clumpy consistency, is not free flowing and has a broad particle size distribution. The product cannot be screened completely through a 90 μm screen. The product contains 44% tin and 13.9% fluorine.

We claim:

1. A method for the synthesis of fine particulate of organic organic tinflourides and organic tinoxyflourides by reacting mono-organic or diorganic tin oxides or hydroxides with hydrofluoric acid, comprising the step of reacting the oxides or hydroxides with the acid in presence of a surface active compound.

2. The method of claim 1, wherein, as the surface active compound, wetting agents having rapid wetting capabilities and stability towards hydrofluoric acid are used.

3. The method of claim 2, wherein, as the surface active compound, fluorinated surfactants, silane surfactants or fatty alcohol or nonylphenol alkoxylates are used.

4. The method of any of claims 1, 2 or 3, wherein the surface active compounds are used in an amount of 0.01 to 0.5% by weight based on the amount of water used.

5. The method of claim 3, wherein the surface active compounds have a content of ethyleneoxide, propyleneoxide or both from 6 to 12.

6. The method of any of claims 1, 2 or 3 for the synthesis of fine particulate alkyl tin fluorides, suitable for the pyrolytic production of fluorine-doped tin oxide layers on glass, glass ceramic and enamel, wherein organic tin compounds, as starting materials, have an average particle size and upper particle size limit which lies below the desired corresponding values of the end product.

\* \* \* \* \*